(12) United States Patent
Ramanathan

(10) Patent No.: US 10,953,194 B2
(45) Date of Patent: Mar. 23, 2021

(54) AORTIC VALVE NO EXCHANGE CATHETER

(71) Applicant: ProMedica Health System, Inc., Toledo, OH (US)

(72) Inventor: P. Kasi Ramanathan, Ottawa Hills, OH (US)

(73) Assignee: PROMEDICA HEALTH SYSTEM, INC., Toledo, OH (US)

(*) Notice: Subject to any disclaimer, the term of this patent is extended or adjusted under 35 U.S.C. 154(b) by 114 days.

(21) Appl. No.: 15/907,456

(22) Filed: Feb. 28, 2018

(65) Prior Publication Data

US 2018/0256848 A1 Sep. 13, 2018

Related U.S. Application Data

(60) Provisional application No. 62/469,624, filed on Mar. 10, 2017.

(51) Int. Cl.
| | |
|---|---|
| *A61M 25/00* | (2006.01) |
| *A61M 25/01* | (2006.01) |
| *A61M 25/09* | (2006.01) |
| *A61F 2/24* | (2006.01) |
| *A61M 5/00* | (2006.01) |

(52) U.S. Cl.
CPC .... *A61M 25/0026* (2013.01); *A61M 25/0108* (2013.01); *A61M 25/0136* (2013.01); *A61M 25/09* (2013.01); *A61F 2/2427* (2013.01); *A61F 2/2436* (2013.01); *A61M 5/007* (2013.01); *A61M 2025/0002* (2013.01); *A61M 2025/0004* (2013.01); *A61M 2025/0006* (2013.01); *A61M 2205/502* (2013.01); *A61M 2230/30* (2013.01)

(58) Field of Classification Search
CPC ............ A61M 25/0029; A61M 25/003; A61M 25/0136; A61M 25/0141; A61M 2025/0002; A61M 2025/0063; A61M 2025/0006; A61F 25/2427; A61F 25/2436; A61F 25/0105; A61F 25/06
See application file for complete search history.

(56) References Cited

U.S. PATENT DOCUMENTS

| | | |
|---|---|---|
| 4,777,951 A | 10/1988 | Cribier et al. |
| 4,901,731 A | 2/1990 | Millar |
| | (Continued) | |

FOREIGN PATENT DOCUMENTS

WO 3949773 A2 10/1999

*Primary Examiner* — Nathan R Price
*Assistant Examiner* — Tania Ismail
(74) *Attorney, Agent, or Firm* — Michael E. Dockins; Shumaker, Loop & Kendrick, LLP

(57) ABSTRACT

A medical device and use thereof provide percutaneous access to a targeted site within a living body, for example the left ventricle of the heart. The device includes an inner tubular member, outer tubular member, and an adjustable control handle. The control handle can precisely control the relative position of the inner tubular member relative to the outer member by providing feedback to the operator. This feedback provided by the control handle allows the operator to precisely maneuver the catheter within a body and change the shape of the catheter system without taking his/her eyes off the task that he/she is performing. The control handle is designed to precisely change the catheter system from one tip shape to another tip shape and back.

20 Claims, 10 Drawing Sheets

(56) References Cited

U.S. PATENT DOCUMENTS

| | | | |
|---|---|---|---|
| 5,383,852 A | 1/1995 | Stevens-Wright | |
| 5,427,114 A | 6/1995 | Colliver et al. | |
| 5,666,970 A | 9/1997 | Smith | |
| 6,190,360 B1* | 2/2001 | Iancea | A61F 2/95 |
| | | | 604/164.09 |
| 6,554,794 B1 | 4/2003 | Mueller et al. | |
| 6,616,597 B2 | 9/2003 | Schock et al. | |
| 7,229,403 B2 | 6/2007 | Schock et al. | |
| 7,717,854 B2 | 5/2010 | Mann et al. | |
| 8,613,706 B2 | 12/2013 | Langston | |
| 8,715,195 B2 | 5/2014 | Ziv | |
| 9,149,230 B2 | 10/2015 | Caron et al. | |
| 9,332,914 B2 | 5/2016 | Langston | |
| 9,504,392 B2 | 11/2016 | Caron et al. | |
| 10,532,193 B2* | 1/2020 | Fischer, Jr. | A61M 25/007 |
| 2005/0203425 A1 | 9/2005 | Langston | |
| 2008/0027334 A1 | 1/2008 | Langston | |
| 2009/0024084 A1 | 1/2009 | Khosla et al. | |
| 2010/0094393 A1 | 4/2010 | Cordiero et al. | |
| 2011/0009699 A1* | 1/2011 | Slenker | A61B 1/00091 |
| | | | 600/123 |
| 2014/0031797 A1 | 1/2014 | Cohen et al. | |
| 2014/0187933 A1 | 7/2014 | Langston | |
| 2014/0236120 A1 | 8/2014 | Tsai et al. | |
| 2015/0119853 A1 | 4/2015 | Gainor et al. | |
| 2015/0223955 A1 | 8/2015 | Li et al. | |
| 2015/0257878 A1* | 9/2015 | Lane | A61F 2/2436 |
| | | | 623/2.19 |
| 2015/0320330 A1* | 11/2015 | Sparks | A61N 1/057 |
| | | | 600/375 |
| 2016/0095523 A1 | 4/2016 | Langston | |

\* cited by examiner

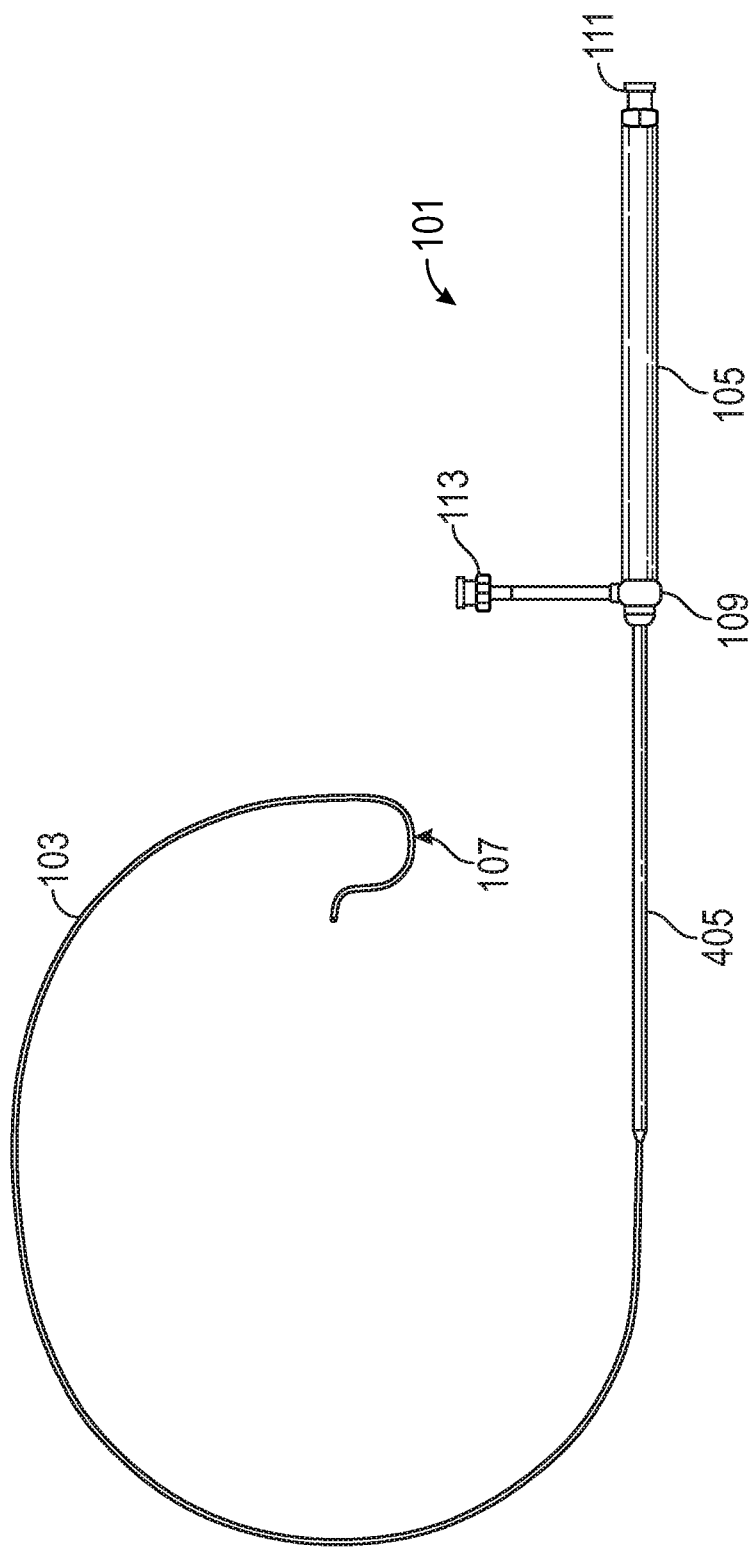

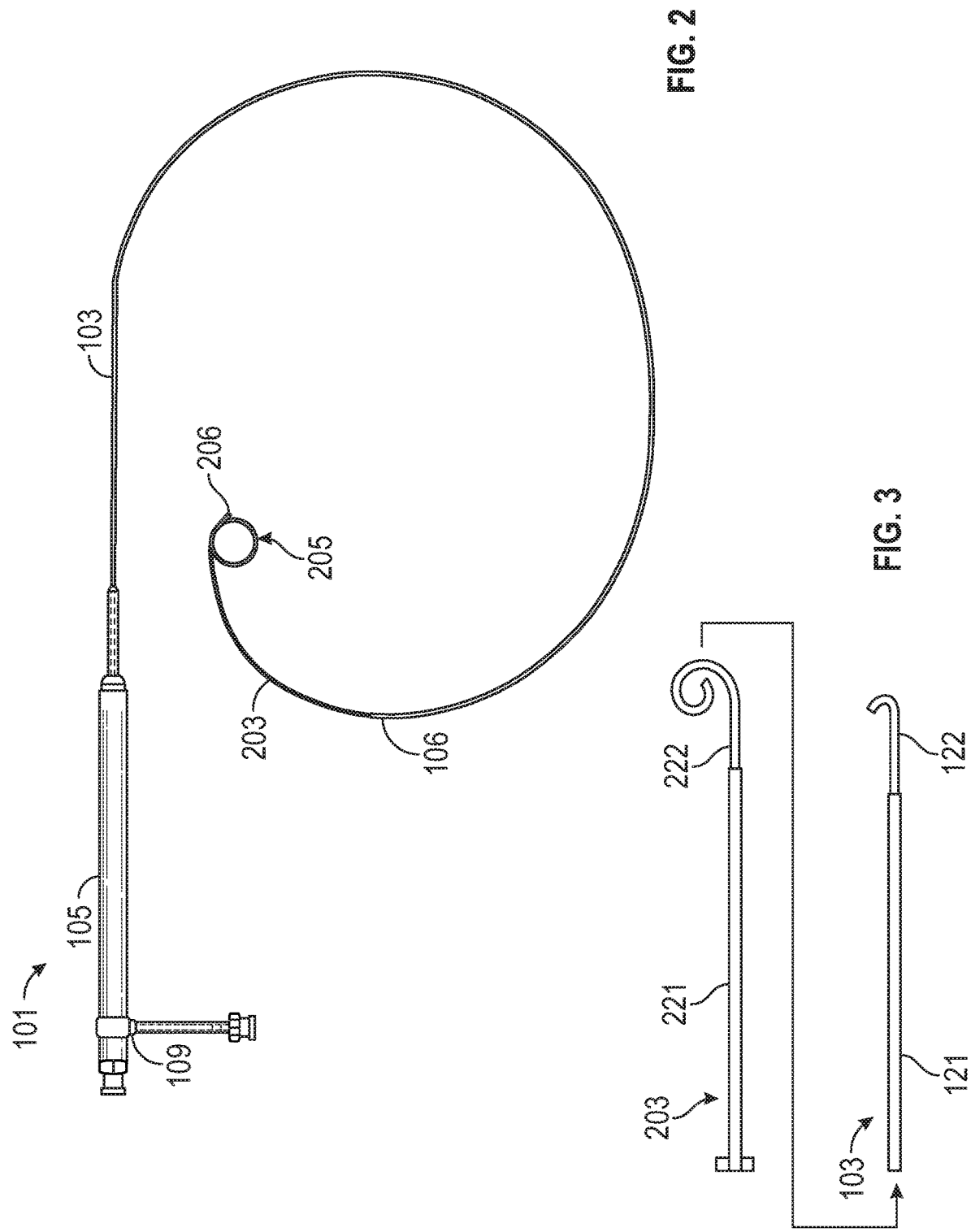

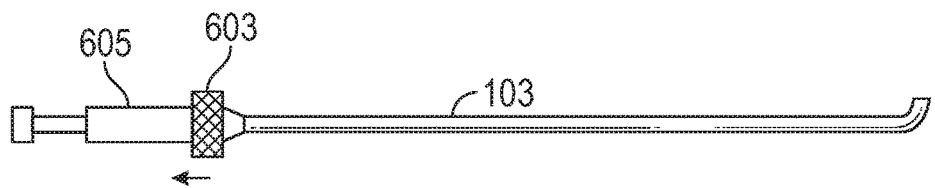
FIG. 5A
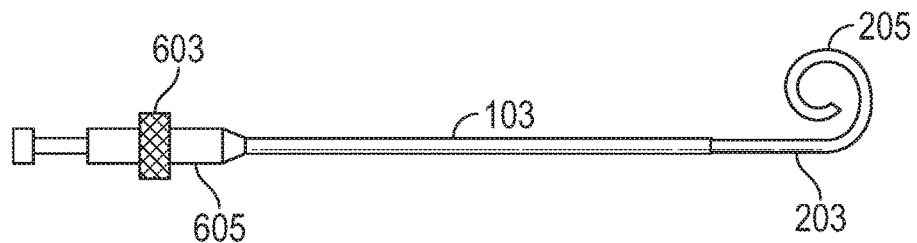
FIG. 5B
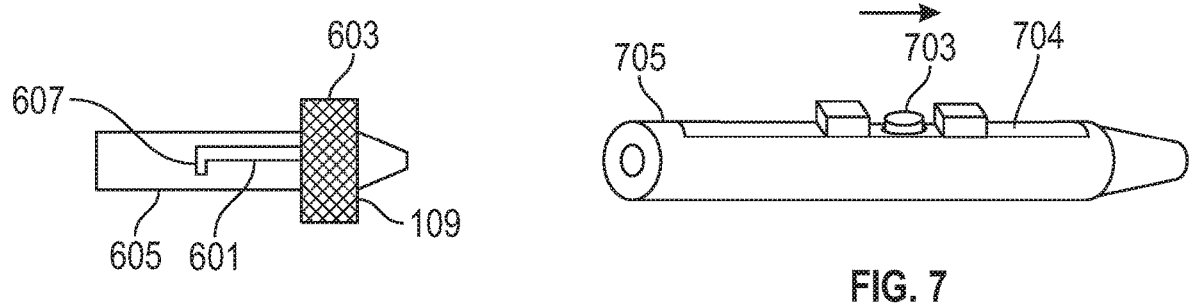
FIG. 6
FIG. 7
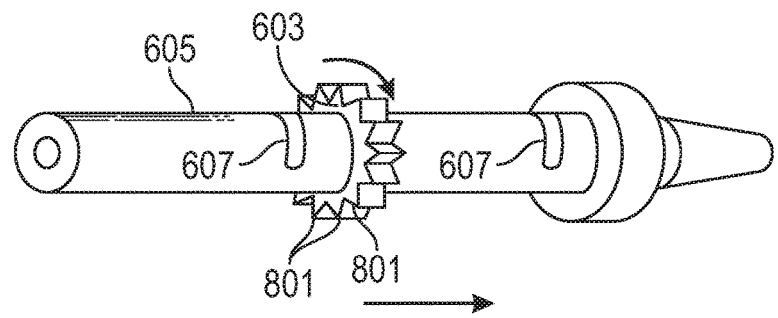
FIG. 8

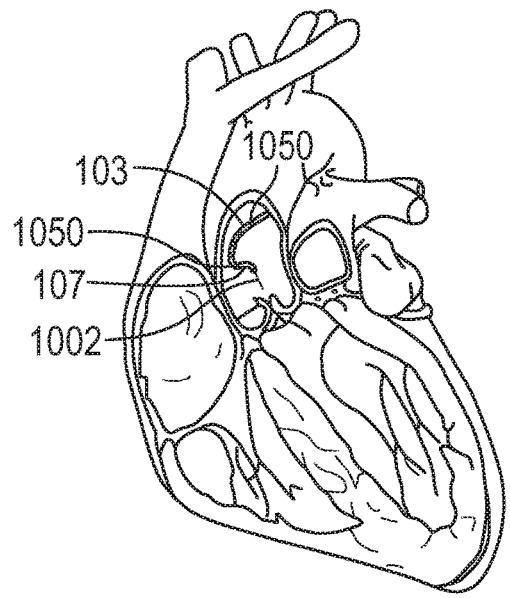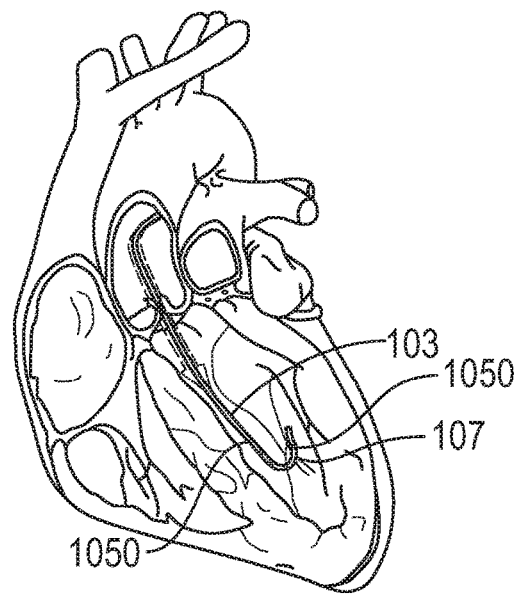
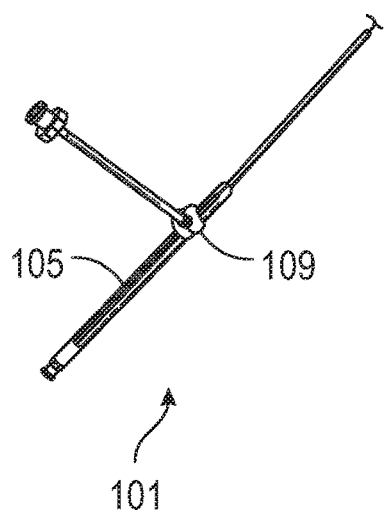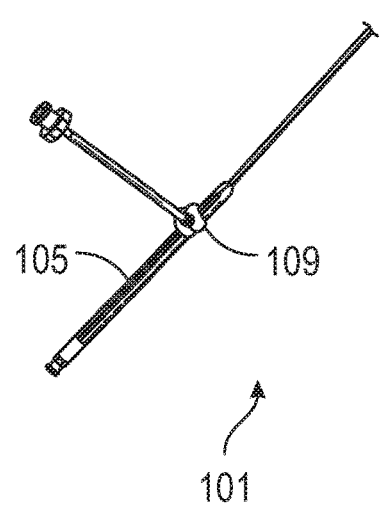
FIG. 10B　　　　　　　　　　FIG. 10C

AORTIC VALVE NO EXCHANGE CATHETER

CROSS-REFERENCE TO RELATED APPLICATIONS

This application claims the benefit of the priority date of U.S. Provisional Patent Application Ser. No. 62/469,624, titled AORTIC VALVE NO EXCHANGE CATHETER, filed Mar. 10, 2017.

BACKGROUND

Field

This present disclosure relates generally to the field of devices used to gain vascular access to organs within a living body and, more particularly, to a concentric dual-member catheter device which allows precise positioning and tip shape change of a catheter used in transcatheter aortic valve replacement procedures while minimizing distractions to the operator.

Discussion

While there are different methods to gain access to internal organs in the body to perform a medical procedure, less invasive approaches using catheters and guidewires delivered through the body's vascular system have become widespread. Minimally invasive procedures offer improved patient outcomes, often with fewer complications and shorter recovery periods. Consequently, increasingly complex percutaneous interventional procedures have been developed to treat various diseases.

In treating heart disease, for example, the use of guidewires and catheters has a long-established history of use. Initially, percutaneous coronary interventions (PCI) were often directed at diagnosing and treating blocked vessels within the heart. More recently, technologies to treat structural heart disorders have been developed and are now part of an interventionalist's armamentarium. Interventional structural heart technologies are comparatively complicated devices requiring advanced techniques to perform the procedure. For example, in Transcatheter Aortic Valve Replacement (TAVR) procedures, a prosthetic valve mounted on a stent is delivered via a catheter, over a guidewire, for placement over a patient's native valve apparatus.

The TAVR procedure is indicated for patients with severe aortic stenosis who may be intermediate or high risk for valve replacement surgery. The number of TAVR procedures has grown rapidly, year over year, as physicians and patients have chosen this minimally invasive approach over more traditional open chest, arrested heart procedures requiring a bypass pump. In order to perform a TAVR procedure, the interventionalist must first access the left ventricle.

Tools to gain access to the left ventricle exist, however, they are not ideal. There are numerous steps needed in a TAVR procedure prior to delivering the replacement valve. Developing improved technologies to combine needed steps can reduce procedural risks associated with multiple device exchanges. These risks include perforation of the heart or vessels and introduction of emboli resulting in stroke. There are other potential complications. The advanced techniques and the high level of concentration required to successfully perform a TAVR procedure highlights an unmet need to reduce device exchanges as much as possible to shorten and simplify the procedure in order improve to patient outcomes.

In improving intravascular procedures, Stevens (U.S. Pat. No. 3,503,385) discloses a vascular diagnostic catheter with an embedded control wire, spanning from the catheter tip to a proximal (near) handle. The control mechanism attached to the handle then manipulates the distal (far) tip of the catheter to form different curves. While this solution enables changing the shape of the distal end of a catheter, it is a costly solution that reduces space efficiency because of the need to have pull wires and the required lumens in a catheter shaft to house the pull wires.

Wittes, et al. (U.S. Pat. No. 3,680,562) describes a catheter with an inwardly curved tip, like a pigtail, with a series of ports aligned longitudinally. A hollow piercing member is inserted to straighten the curved tip to facilitate delivery. There are other devices that similarly change shape using a stiff insertable member into the catheter. This device and others, which utilize a stiffening insert to change the shape of the distal end of the catheter, add steps to the procedure. The stiffening element must be inserted and withdrawn to achieve a shape change. In a complex procedure performed in a setting with many distractions, there is a need for the operator to be able to manipulate the catheter distal tip from an initial configuration to a final configuration quickly and easily, without taking undue attention and effort.

Pigtail shaped diagnostic catheters have long been used in intravascular medical procedures. They can be used to infuse imaging agents or drain fluid from organs. In addition, the pigtail configuration can be used to sheath a guidewire, offering protection against injury caused by a guidewire. The curved pigtail shape can have multiple loops which deflect the guidewire away from vulnerable tissue. Pigtail catheters, however, are not ideally shaped to traverse the vasculature to reach hard to access areas in the body. Pigtail catheters must often be exchanged with other guiding catheters more suitably shaped to reach a precise target location in the body. Making catheter exchanges often entails the need to exchange guidewires, further complicating the procedure.

U.S. Pat. No. 4,033,331 describes the use of a wire to shape the tip of a catheter. The wire, which fills the internal lumen of the catheter, then must be extended or retracted to change the shape of the distal end. This method of catheter tip shaping can involve many steps. There is a need for a device which more efficiently reduces the steps needed to perform a procedure.

U.S. Pat. No. 5,120,323 discloses a telescoping guide catheter system comprised of an inner and outer guide catheter, neither of which is pre-curved. US20070021732A1 describes an inner guiding introducer and an outer guiding introducer to access the left ventricle. Both the inner and outer members are pre-curved. However, both systems lack a means to precisely control retraction and extension of the inner member relative to the outer member.

U.S. Pat. No. 4,960,134A describes a catheter with a symmetrical cylindrical control handle and a flexible catheter tip. The control handle comprises a housing having a piston chamber. A piston is mounted in the piston chamber and can move lengthwise. The proximal end of the catheter body is fixedly attached to the distal end of the piston. A pull wire is attached to the housing and extends through to the catheter tip. Lengthwise movement of the piston relative to the housing results in deflection of the catheter tip. While a control mechanism enables precise tip deflection, the use of pull wires through a catheter using a dedicated lumen precludes a space efficient and cost effective solution.

U.S. Pat. No. 5,666,970A describes a control mechanism for manipulating the shape of the catheter and providing a rotational locking mechanism. This solution describes multiple moving elements, including a biasing member to control catheter movement. This complex solution requires a large housing, which makes it impractical to miniaturize and expensive to manufacture.

In US20150119853A1, Gainor describes a convertible shape catheter and method of use that includes the use of two catheters designed to work in tandem, one inside the other, to achieve any number of catheter distal tip shapes to advance through the anatomy and provide for a pigtail configuration. This unlimited range of adjustments becomes a hindrance in a procedure on a frail patient, where longer procedures are associated with serious complications such as renal failure due to the excessive use of imaging contrast and patient dehydration. For this design, catheter manipulation to change from an initial to a final orientation requires fluoroscopic visual guidance, with contrast media injections. This task may require a degree of operator concentration and extended manipulation that obviates any purported advantages.

In diagnosing and treating circulatory diseases it can be advantageous to measure differential pressure within a living body. For example, the differential pressure can be measured across the aortic valve to quantify the severity of the stenoses affecting blood flow from the heart to other organs.

There are intravascular catheter devices in the prior art that utilize the means to make two pressure measurements to measure differential pressure within a living body. Such prior art patents include U.S. Pat. Nos. 6,616,597B2, 7,229,403B2, 5,427,114A, 4,901,731A, 7,717,854B2.

In U.S. Pat. No. 4,777,951A, Cribier et al., taught the use of measuring differential pressure across the aortic valve using a balloon catheter to confirm diagnosis of calcified aortic valve stenosis and to treat the condition via dilation of the valve orifice by inflating the balloon within the stenotic valve. The effect of the balloon inflations to dilate the stenotic region could be measured by the pressure drop across the aortic valve annulus, when measured from the left ventricle across the obstructed valvular apparatus and into the aorta. This differential pressure could be measured sequentially after successive balloon inflations to measure the effect of balloon dilation to achieve some endpoint that presumably relieves symptoms of the disease. Importantly, measuring differential pressure requires simultaneous pressure readings from two areas such as between the left ventricle and the aorta. The use of a balloon to enlarge the aortic valve orifice, while still performed, has been largely supplanted by a catheter based approach to implant a prosthetic valve apparatus over the native valve. This new procedure would benefit from a device better integrated into the workflow of the currently practiced procedure.

In U.S. Pat. No. 9,332,914B2, Langston proposed the use of a dual lumen pigtail catheter, one lumen placed in the left ventricle and the other exposed to the aorta, to measure differential pressure across the aortic valve to diagnose aortic valve stenosis. This device does not facilitate a seamless transition to a therapeutic transcatheter aortic valve procedure, hence adding to a workflow that is already demanding of the operator.

There remains an unmet need for a device to provide for differential pressure measurements, or any two channel sensor measurements to interrogate the circulatory system function, better optimized to facilitate today's complex interventional procedures by eliminating or combining steps in a difficult procedure requiring high levels of concentration routinely performed on frail patients.

The utilization of these prior art devices is compromised by size, complexity, difficulty of use, lack of utility and cost.

In addition, handle control mechanisms current available offer a limited range of motion. Catheter handles offering steering capability also tend to be large in diameter, compromising their utility. Consequently, there remains a need for a device that can facilitate access to a precise location within the body, enable an easy and fast catheter shape change, and provide for measuring differential pressure within vasculature across an obstructed and diseased valve in a cost and space efficient manner.

Other procedures are similarly compromised. Techniques currently used to facilitate PCIs include the concept of a parent-child catheter, with an inner catheter being inserted through an outer guide catheter to provide additional support in complex PCI procedures where a balloon or stent backs out of the target position. In this case an inner catheter is inserted through a guide catheter to provide additional support. Currently, this parent-child catheter arrangement requires two separate catheters. There is a need to simplify the procedure needed to provide additional support during PCI procedures.

Another interventional procedure in need of improvement includes radial artery cardiac catheterization. This technique is increasing in use and there is a need for specialized radial catheters to improve the workflow and procedure. One of the keys for radial catheterization is to reduce the number of catheter exchanges in order to reduce radial artery spasm. Currently there exists single catheters for this procedure, but they have very aggressive shapes, wildly contoured at the tips, that could potentially lead to dissection of the coronary vessel.

SUMMARY

The disclosed invention provides for a time saving medical device for use in medical procedures, such as transcatheter valve replacements, that offers a combination of features which reduces the number of medical devices needed to perform the procedure while offering both diagnostic function and procedure time savings in seamlessly transitioning from a diagnostic procedure to a therapeutic procedure. Another advantage of this invention is that the patient and lab personnel will be exposed to less radiation. This will also have the potential to make the procedure safer. This device offers to save the healthcare system costs associated with the use of extra devices and the time needed to perform numerous device exchanges now required to safely perform a procedure, such as a TAVR procedure.

The invention is a catheter system comprised of an inner and an outer tubular member with an attached control handle mechanism. The inner tubular member and outer tubular member are also referred to as the inner and outer catheters. The outer tubular member can be advanced or retracted relative to the inner tubular member, the advancement or retraction controlled by a control handle mechanism. The inner and outer tubular member are pre-curved or, in other words, processed into a non-linear shape. It is also anticipated that one or more of the catheters can be straight and still benefit from this invention. The control handle is designed to provide precise and repeatable movement of the outer tubular member relative to the inner tubular member. This permits easy changes in catheter form minimizing the effort needed by the operator to make device changes while performing the procedure.

The inner tubular member has the resilience to adapt to the pre-curved shape of the outer tubular member when the outer tubular member is extended over the distal tip of the inner tubular member. This shape change feature facilitates safe and easy access to a treatment site, providing for an initial configuration optimized to access the treatment site and a second configuration optimized for use at the treatment site. This system is designed to eliminate a catheter exchange and the need for multiple guidewire exchanges used to facilitate catheter exchanges.

The device includes a relatively long inner tubular member as compared with the outer tubular member. The outer tubular member can be extended completely over the distal tip of the inner tubular member. The outer tubular member is constructed with a stiffness that conforms the shape of the inner tubular member to that of the outer tubular member. The distal end of the outer tubular member is shaped to optimize access to the left ventricle or another target site. A control handle enables precise and repeatable movement of the outer tubular member resulting in a shape change from an initial tip shape configuration to a final tip shape configuration, by exposing the inner tubular member without distraction or undue manipulation. This is accomplished by permitting a defined range of travel that is governed by a distal stop, a movable range and a proximal stop. This predefined range of motion enables the operator to make tip shape changes easily and without the need for fluoroscopic visual confirmation and without the need for the operator to visually observe the handle when making a change.

The invention may also be configured to deliver devices into other areas of the body, for example, into the left atrial chamber of the heart through a septal puncture, or into coronary arteries. More broadly, this invention can replace numerous devices needed to gain access to a specific location in the anatomy. The position of the control handle distal stop, allowable range of motion, and proximal stop are adjusted to suit a specific application. It may also be advantageous to reverse the direction of the catheter system movement from retracting the outer catheter, or outer tubular member, to expose the inner catheter to extending an inner catheter past the end of the outer catheter.

The control handle precisely controls the shape change of the catheter in repeatable manner. The range of motion of the outer tubular member is constrained. This is controlled by the allowable travel designed into the handle. In limiting the range of relative positioning, the operator can easily facilitate a fast exchange, in a controlled manner, from an initial configuration to a final configuration. A positive lock and/or detent mechanism is incorporated into the control handle to secure the device in its intended configuration until the operator desires to change the catheter distal shape. The handle control mechanism has been optimized to provide a long range of movement in a small space efficient package.

The outer tubular member may have a side port configured to fluidly communicate with the lumen of the outer tubular member. In this way, the lumen can be flushed with saline or other fluids. A vacuum can also be applied through the side port to remove air or other gas bubbles from the lumen of the outer tubular member to prevent air ingress into the blood circulation system.

A pressure transducer or a separate port engaged with a pressure transducer can be connected to the outer tubular member side port. The side port described may have a threaded interface to ensure a secure and leak-free connection to other accessories. In another embodiment, the pressure sensor can be mounted near or at the distal end of the outer tubular member to make a more direct measurement of blood pressure. This overcomes any deleterious dampening effects from trying to measure pressure through a small lumen in a catheter. In other words, the pressure signal weakens over distance making the signal to noise ratio worse. In another embodiment a dedicated lumen may be incorporated into the space between the outer and inner tubular member to provide a channel for blood to be in fluid communication with an external pressure sensor, the dedicated lumen reducing any pressure dampening effects that a small clearance between tubular members might create. In still another embodiment, a micro-electronic mechanical (MEMs) pressure sensor may be integrated at the end of the outer tubular member to provide high fidelity pressure measurements.

An access port is attached to the proximal most portion of the inner tubular member to enable delivery of other devices such as guidewires or fluid such as sterile saline. Alternatively, a pressure transducer or a separate port engaged with a pressure transducer can be connected to the proximal port. The proximal port described may have a threaded interface to ensure a secure and leak-free connection to other accessories or to fluids.

The control handle can incorporate O-rings or other sealing means to seal the lumen of the outer catheter while still preserving its ability to be slid over the inner elongate tubular member. The O-rings or sealing means can be incorporated into a housing that also serves to retract and, subsequently, advance the outer tubular member over the inner tubular member.

To enhance safety, the control handle is configured to retract the outer tubular member, rather than extend the inner tubular member. This safety feature is provided to prevent injury within the left ventricle. For example, there are vulnerable structures such as papillary muscles, chordae tendineae, mitral valve leaflets, and others, that can be damaged by inadvertent extension of the catheter.

Additional features of the presently disclosed methods and devices will become apparent from the following description and appended claims, taken in conjunction with the accompanying drawings.

BRIEF DESCRIPTION OF THE DRAWINGS

FIG. 1 is an illustration of the invention in its initial configuration showing an outer tubular member in an AL1 catheter tip configuration;

FIG. 2 is an illustration of the invention with an inner tubular member forming a pigtail configuration at the distal end, extending from within the outer tubular member after manipulating the control handle to change the tip shape;

FIG. 3 is an exploded-view illustration of the inner and outer tubular members in component form shown separated for clarity;

FIG. 5A is an alternative embodiment of the invention in initial configuration showing tip shape and handle position;

FIG. 5B is an alternative embodiment of the invention in second configuration showing tip shape and handle position;

FIG. 6 is an illustration showing an alternative embodiment of a portion of the control handle;

FIG. 7 is an illustration showing an alternative embodiment of a control handle configuration with a spring-loaded detent system actuated by a depressible release button;

FIG. 8 is an illustration showing an alternative embodiment of a control handle with undulations on the outer surface of the circular control ring;

DETAILED DESCRIPTION OF THE EMBODIMENTS

Figure 4:
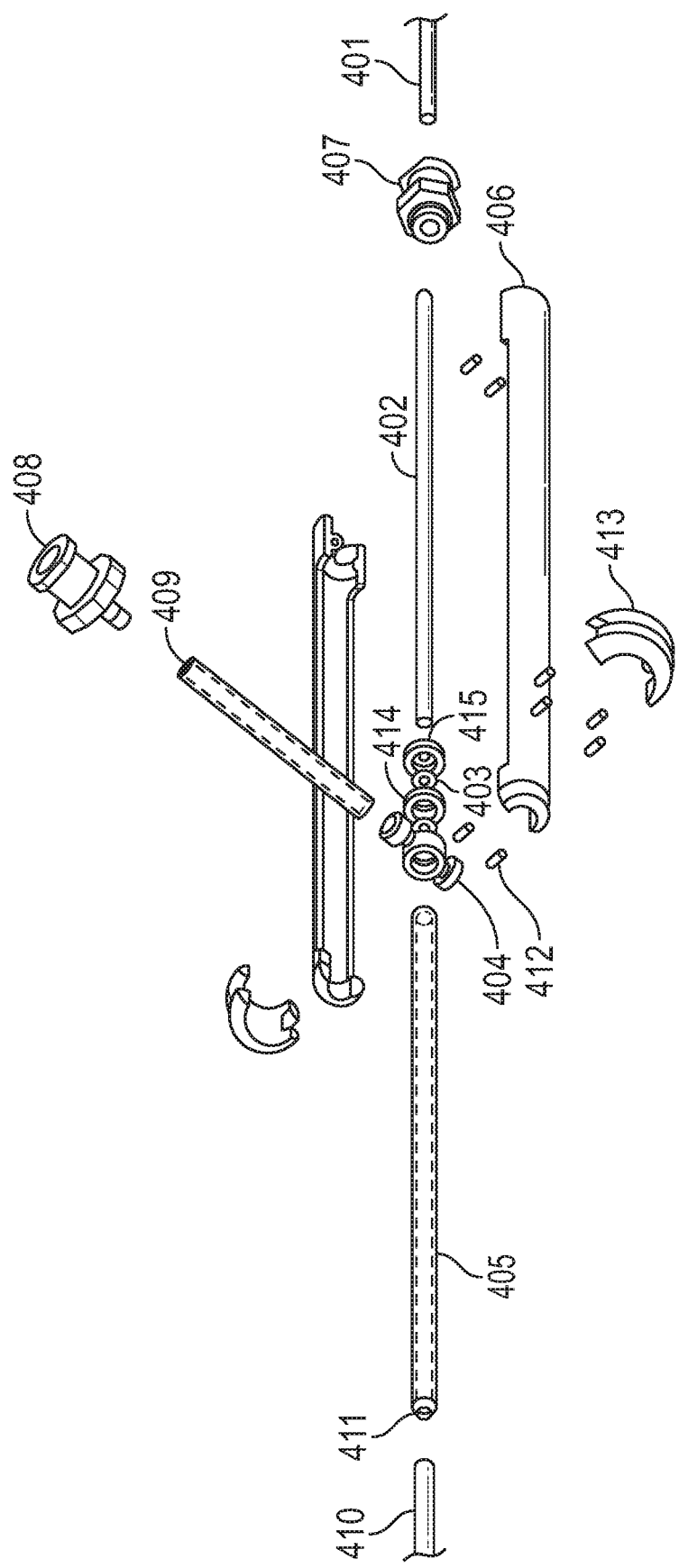
FIG. 4 is an exploded-view illustration of the control handle.

The following discussion of the embodiments of the disclosure directed to an aortic valve no exchange catheter system is merely exemplary in nature, and is in no way intended to limit the disclosed techniques or their applications or uses.

Shown in FIG. 1 is the invention, which is a no exchange catheter system 101 that benefits by reducing the need to remove and exchange various catheters and guidewires during a medical procedure. Shown in FIG. 2 is the no exchange catheter system 101, comprised of an inner tubular member 203 within an outer tubular member 103 each attached to separate components of a control handle 105 approximately at their proximal ends. As discussed herein, the outer tubular member 103 is slidably extensible and retractable over the inner tubular member 203, controlled by the components of the control handle 105.

The inner tubular member 203 is longer than the outer tubular member 103. In exemplary fashion, an inner tubular member 203 may have a pigtail shape 205 at its distal end 206, and may be "5F" (meaning 5 on the French scale, which equates to a diameter of 1.667 mm), and 110 cm long. The outer tubular member 103 may have an AL1 (a particular type of tip) shape at its distal end 107, and can be 6F (2 mm diameter), and is 90 cm long. Other lengths and diameters are contemplated. For example, the total catheter length can be 125 cm and the range of movement of the outer tubular member 103 over the inner tubular member 203 can be 12 cm. For transcatheter aortic valve replacement procedures, the standard guidewire length of 260 cm dictates the total catheter system length be less than 130 cm, and preferably close to 130 cm. Other tip shapes may also be used as best suited for a particular application.

The control handle 105, at the proximal end of the catheter system 101, has a circular control ring 109 to facilitate movement of the outer tubular member 103. When the operator pulls back the outer tubular member 103 via sliding the circular control ring 109 back on the control handle 105, the distal end of the inner tubular member 203 is exposed and forms a pigtail shape when fully extended from the outer tubular member 103. The linear range of motion of the outer tubular member 103 can be 10 to 20 cm. Other distal inner tubular member shapes are contemplated and can be similarly exposed when the outer tubular member 103 is retracted. Likewise, the range of linear travel for the outer tubular member 103 can be optimized for other contemplated applications such as converting a Judkins left catheter to a Judkins right catheter and utilizing a range of travel that is less than 10 cm. Alternatively, other applications may dictate a larger than 20 cm range of travel.

Figure 11:
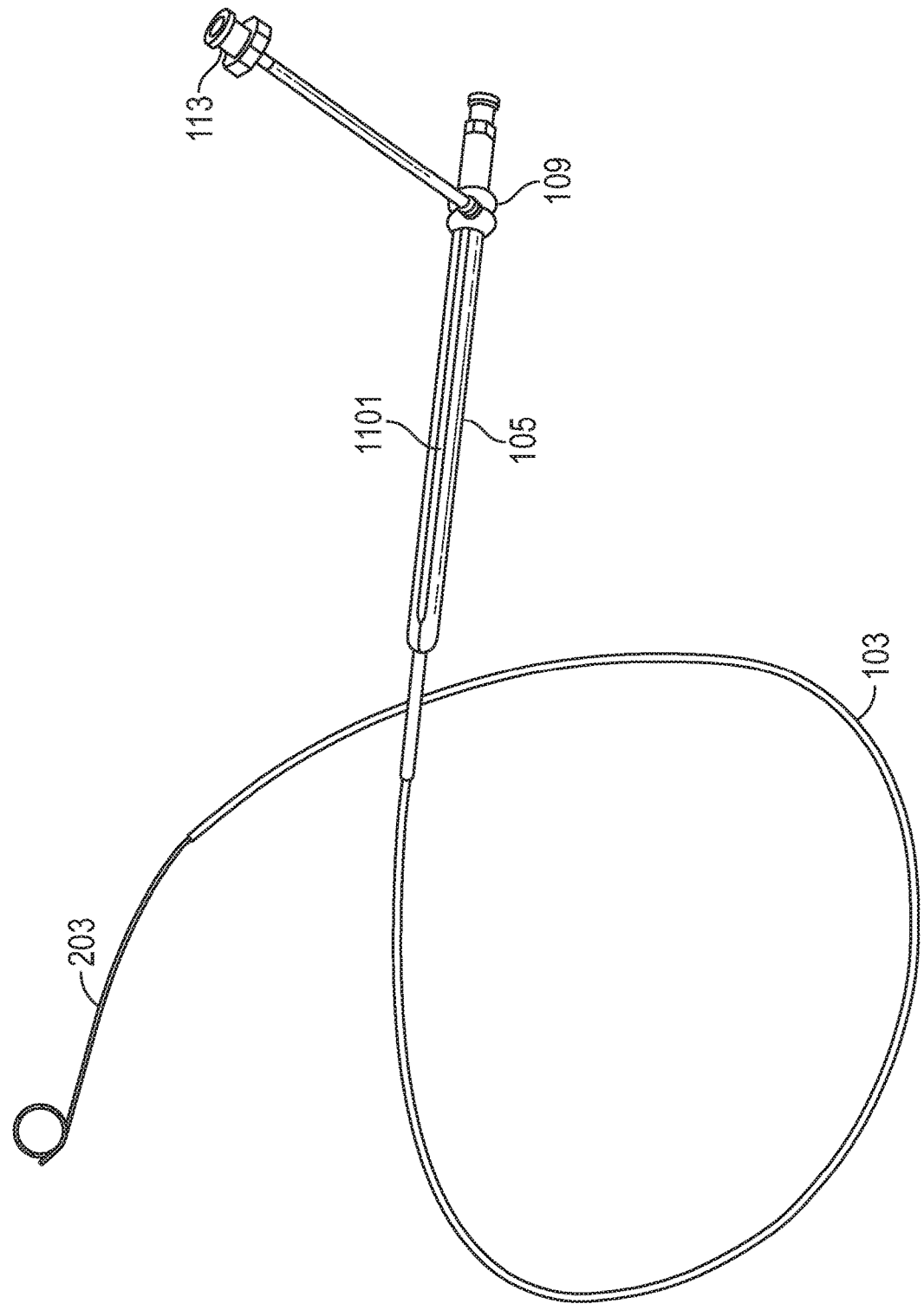
FIG. 11 is an illustration of the invention shown with a view of the slot in the control handle mechanism that limits movement of the outer tubular member.

By design, the control handle 105 limits travel of the circular control ring 109 and thus the travel of the outer tubular member 103 over the inner tubular member 203. This is controlled in one embodiment by the dimensions of a slot 1101 in the control handle 105 as shown in FIG. 11. In some embodiments of the invention, a control ring locking feature is used to temporarily fix the position of the outer tubular member 103 relative to the inner tubular member 203, where the catheter shape can be locked into position only when the outer tubular member 103 is fully extended or fully retracted. Referring to FIG. 6, a slot segment 607 extending 90 degrees from a longitudinal travel slot 601 is provided to immobilize a circular control ring 603 at the extreme limit of the circular control ring travel. The circular control ring 603 performs the same function as the circular control ring 109—that is, controls the position of the outer tubular member 103 relative to the inner tubular member 203. When at either of two extreme positions, the circular control ring 603 can be rotated to lock the position of the catheter. In FIG. 6, the control ring 603 covers another of the slot segments 607 which is at the distal end of the longitudinal slot 601. Alternatively, the slot 1101 of FIG. 11 or a hard stop (not shown) built into the handle can preclude axial movement, forward and backwards, in place of a twist lock mechanism.

The circular control ring 603 is shown in FIG. 6 as having a knurled outer surface. FIG. 8 shows a control ring with outward facing undulations 801 or other features designed to enhance grip for operators wearing gloves.

FIG. 1 depicts the device in the initial configuration, shown here as an Amplatzer AL1 tip shape. Alternatively, the shape of the distal segment may be that of an Amplatzer AL2 or any other shape an operator prefers to gain access to a particular area of the anatomy. The outer tubular member 103 has been extended to cover the distal end of the inner tubular member 203 (thus the inner tubular member 203 is not visible in FIG. 1), and the distal tips of the inner tubular member 203 and outer tubular member 203 are aligned. In this position, the distal shape of the catheter is governed by the shape of the outer tubular member 103. A luer 111 is fused to the proximal most edge of the inner tubular member 203, thereby allowing a fluidic coupling to the proximal end of the inner tubular member 203. The fluidic coupling provided by the luer 111 may be used to monitor pressure in the inner tubular member 203, or deliver a fluid through the inner tubular member 203, for example. In FIG. 1, the circular control ring 109 is in its distal most position, relative to the handle 105; this position of the circular control ring 109 is what causes the outer tubular member 103 to be fully extended over the inner tubular member 203.

A side port assembly 113 is attached to the circular control ring 109 and is able to fluidly communicate with the space between the inner tubular member 203 and the outer tubular member 103, regardless of the position of the circular control ring 109. The fluid communication space is sealed using O-rings or other sealing means, discussed below. The O-rings are designed to slide along with the circular control ring 109.

FIG. 2 depicts the device with the pigtail section 205 shown at the distal end 206 of the inner tubular member 203. In this configuration, the outer tubular member 103 has been fully retracted to expose the distal end of the inner tubular member 203. The inner tubular member 203 can be longer than the outer tubular member 103. Hence, in this configuration of FIG. 2, a section of the inner tubular member 203 is extended from the outer tubular member 103. The circular control ring 109 is in its proximal most position in this configuration, which is what caused the outer tubular member 103 to retract and expose the portion of the inner tubular member 203. A distal tip 106 of the outer tubular member 103 is denoted on FIG. 2; this is the point at which the inner tubular member 203 emerges from the outer tubular member 103.

FIG. 3 depicts the inner tubular member 203 and the outer tubular member 103 as separated, with each showing an exemplary tip shape. The inner tubular member 203 is made from a relatively flexible polymeric material, one that conforms to the shape of the outer tubular member 103 when inserted into the outer tubular member 103. The polymeric inner tubular member 203 is made from a soft material such as a thermoplastic elastomer. One such soft material is a polyether block amide and has a low durometer value, for example, 35-55 Shore D. An example of the polyether block amide is sold under the trademark PEBAX®. Other polymers such as thermoplastic polyurethanes with similar softness and similar durometer ranges are also contemplated. These materials are well known to those skilled in the art. The wall of the inner tubular member 203 is made deliberately thin, for example in a range of 0.003" to 0.007". The preferred wall thickness is approximately 0.005". The thin wall thickness facilitates shape conformance of the inner tubular member 203 to the outer tubular member 103.

The polymeric outer tubular member 103 is made from a relatively stiffer material than the inner tubular member 203. This can be accomplished using a higher durometer polymer, relative to the inner tubular member 203. A polymeric material such as a polyether block amide in a range of durometers such as 55-76 Shore D are suitable. An example of the polyether block amide is sold under the trademark PEBAX®. Other polymers such as thermoplastic polyurethanes with similar softness and similar durometer ranges are also contemplated.

The stiffness of the individual tubular members can be varied using one or more of several techniques including selecting and/or mixing polymers of differing hardness, adjusting the tubing wall thickness, incorporating a stainless steel braid reinforcement, and/or using a multi-layer tubing design.

Typical intravascular catheters can be comprised of two sections, namely a proximal and distal section. These two sections are fused together to form one complete catheter. However, each section is designed to perform a different function. For example, the first, or proximal section, tends to be straight and stiff to enable advancement of the catheter to a target region. The second, or distal section, is typically softer and shaped to engage the anatomy. It is a common practice to utilize different stiffness grades of the same basic polymer material to fabricate the proximal and distal segments of each tubular member.

The inner tubular member 203 of this invention is comprised of a first section 221 and a second section 222, wherein the first section 221 is a generally elongated straight section which is connected at its distal end with the second section 222, which is a curved section such as a pigtail configuration.

Similarly, the outer tubular member 103 of this invention is comprised of a first section 121 and a second section 122, wherein the first section 121 is a generally elongated straight section which is connected at its distal end with the second section 122 that forms a compound curve designed to easily access the aortic valve and provide passage to the left ventricle. An example of a distal shape may be an Amplatzer AL1.

FIG. 4 shows the major components of the control handle assembly in an exploded view. In short, the handle assembly provides for a slidable and leak free outer tubular member 103 configured to slide over a reinforced inner tubular member 203. The outer tubular member 103 is attached to a control handle mechanism enabling the operator to retract or advance the outer tubular member 103. A distal end 401 of the inner tubular member 203 may be inserted through the handle components for assembly. A stainless steel hypotube 402 is inserted over the inner tubular member 203, is used to reinforce the inner tubular member 203, and functions to prevent unwanted bending or kinking of the inner tubular member 203 during handle manipulation.

A sealing means such as an O-ring, a plurality of O-rings, or a hemostasis valve, adapted for sliding along a stiff, reinforcing member enables relative movement of the inner tubular member 203 and outer tubular member 103 while continuously providing a blood hemostasis seal. O-rings 403 are used to seal the proximal most portion 410 of the outer tubular member 103, which in turn, is fused to a flexible slider tube 405. This ensures a leak free system enabling the inner tubular member 203 and the outer tubular member 103 to be slidable in relation to each other.

A main body 404 within the circular control ring houses the O-rings 403 and provides for a sealed fluid path (dashed line in FIG. 9) from the proximal segment 410 of the outer tubular member 103 to the side port 408. A flexible slider tube 405 is inserted into the proximal segment 410 of the outer tubular member 103. This enables the distal end 401 of the inner tubular member 203 and the stainless steel hypotube 402 to fit within the flexible slider tube 405. An adhesive bond with an adhesive fillet 411 provides a leak-free seal between the flexible slider tube 405 and the proximal segment 410 of the outer tubular member 103 after assembly.

The control handle mechanism housing 406 has a slot (FIG. 11, 1101) providing a fixed range of travel for the control ring 109. The control handle mechanism housing 406 is made in two halves, which when assembled are joined using adhesive or fasteners. The control handle mechanism housing 406 houses the distal end 401 of the inner tubular member 203 and provides the operator with a feature to grip the catheter. A luer 407 is bonded to the proximal end of the inner tubular member 203 and provides a means to couple the inner tubular member 203 to accessories such as a syringe or a Touhy Borst connector (not shown).

The circular control ring 413 (same as control ring 109) is assembled from two halves bonded together and provides the operator with an easy to grip surface to manipulate the position of the outer tubular member 103. The circular control ring 109 attaches to the handle control mechanism 105 as shown in FIG. 1. This assembly, in turn, houses O-rings 403, an O-ring slider mid-body 414, and O-ring slider end cap 415, and maintains the O-rings in position. Dowel pins 412 can be used to fasten the circular control ring halves 413 together immobilizing the components in the circular control ring 109. A side port tubing 409 connects the side port 408 to the proximal segment 410 of the outer tubular member 103, to enable a leak free fluid communication path from the side port 408 (or 113 in FIG. 1) to the outer tubular member 103.

Figure 9:
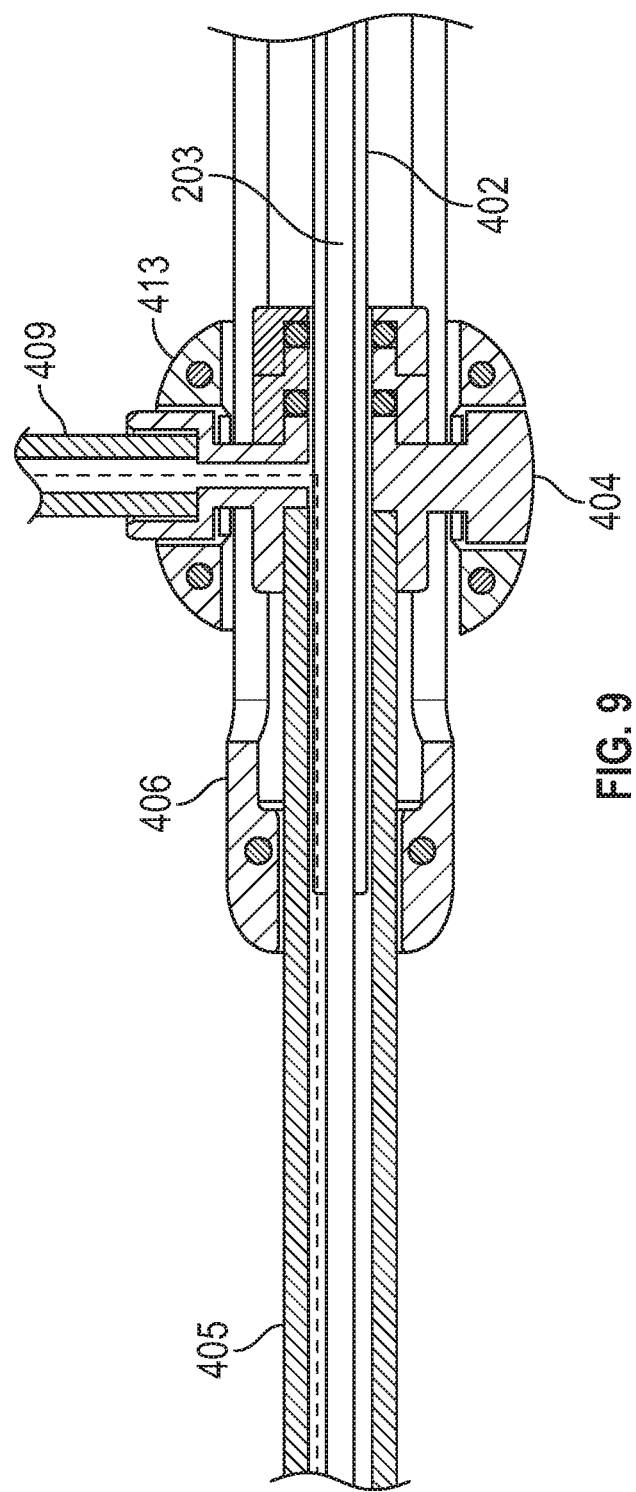
FIG. 9 is a cross sectional illustration showing a view of the control handle, where dashed lines depict a fluid flow path from a side port.

FIG. 9 is a cross-sectional illustration of the control handle assembly showing many of the same elements as FIG. 4. The following discussion is provided to summarize the operation of the tubular members and the control handle assembly as depicted in FIGS. 1, 2, 4 and 9. The key point is that the inner tubular member 203 is fixed relative to the control handle 105, while the outer tubular member 103 slides relative to the inner tubular member 203 based on movement of the control ring 109 along the control handle 105 (FIGS. 1 & 2). After assembly, the inner tubular member 203 is fixed in longitudinal position relative to the control handle 105, which is embodied primarily in the two halves of the control handle mechanism housing 406. The hypotube 402 supports the inner tubular member 203 to prevent kinking, and the luer 407 allows a fluidic coupling to the inside of the inner tubular member 203. The outer tubular member 103 slides longitudinally relative to the inner tubular member 203 and the control handle 105, driven by the position of the control ring 109, which is embodied primarily in the circular control ring halves 413 and the control ring main body 404. The flexible slider tube 405 transfers motion of the control ring 109 to the outer tubular member 103 itself. The flexible slider tube 405 slides over the hypotube 402 within the handle assembly. The annular space between the inner tubular member 203 and the outer tubular member 103 is in fluid communication with the side port tubing 409 and the side port 408, as shown in FIGS. 4 and 9.

FIG. 5a shows a depiction of an embodiment of the currently disclosed catheter system in an initial configuration and FIG. 5b shows the same catheter system in a second configuration. FIGS. 5-8 depict different embodiments than the figures discussed previously, where in particular, the embodiments of FIGS. 5-8 include handle features for locking the extension/retraction position of the outer tubular member 103 relative to the inner tubular member 203, but do not include a side port. FIGS. 5a/b include a control handle 605 and a control ring 603. As in earlier embodiments, longitudinal motion of the control ring 603 along the handle 605 moves the outer tubular member 103 relative to the inner tubular member 203. The position of the control ring 603 is shown in both an initial configuration (FIG. 5a, where the outer tubular member 103 is fully extended over and covers the inner tubular member 203) and a second configuration (FIG. 5b, where the control ring 603 and the outer tubular member 103 have been retracted, exposing the pigtail 205 at the distal end 206 of the inner tubular member 203). The position of the control ring 603 controls the exposed amount of the inner tubular member 203, which in turn correlates to the configuration of the catheter tip, thus providing a visual cue to the operator of the distal tip configuration.

FIG. 6 shows the control handle 605 detached from the catheter. In this embodiment of the control handle mechanism, the range of travel is dictated by a slot 601 in the handle housing. The slot 601 may include a locking feature, a slot segment 607 extending 90 degrees from the longitudinal travel slot 601, at the proximal and distal (not shown) extremes of travel to provide for a twist lock mechanism to immobilize the circular control ring 603 and thus preventing unwanted catheter tip shape changes.

FIG. 7 shows a control handle 705 which includes a spring-loaded detent system actuated by a depressible release button 703 that may provide additional means to lock the catheter into position. The button 703 is a control element which replaces the control ring 603 of FIG. 6, and the outer tubular member 103 is attached to the button 703 for adjustment of the position of the outer tubular member 103. The button 703, when pressed, may move along a slot 704. Releasing the button 703 locks the button 703 in place, which locks the position of the outer tubular member 103 relative to the inner tubular member 203.

FIG. 8 shows the handle 605 with undulations 801 on the outer surface of the control ring 603, rather than the knurled surface of FIG. 6, to enhance the grip of the operator. The arrows in FIG. 8 depict the longitudinal travel of the control ring 603 relative to the handle 605, and rotation of the control ring 603 into the slots 607 at either end of the range of travel.

The handle embodiments of FIGS. 6-8 are shown to illustrate the outer tubular member 103 adjustment and locking features. For the sake of clarity and simplicity, these handle embodiments are not shown with additional features such as the side port 113 and the luer 111 of FIG. 1—but the side port and luer features are equally applicable to any and all handle embodiments, including those of FIGS. 6-8.

Figure 10A:
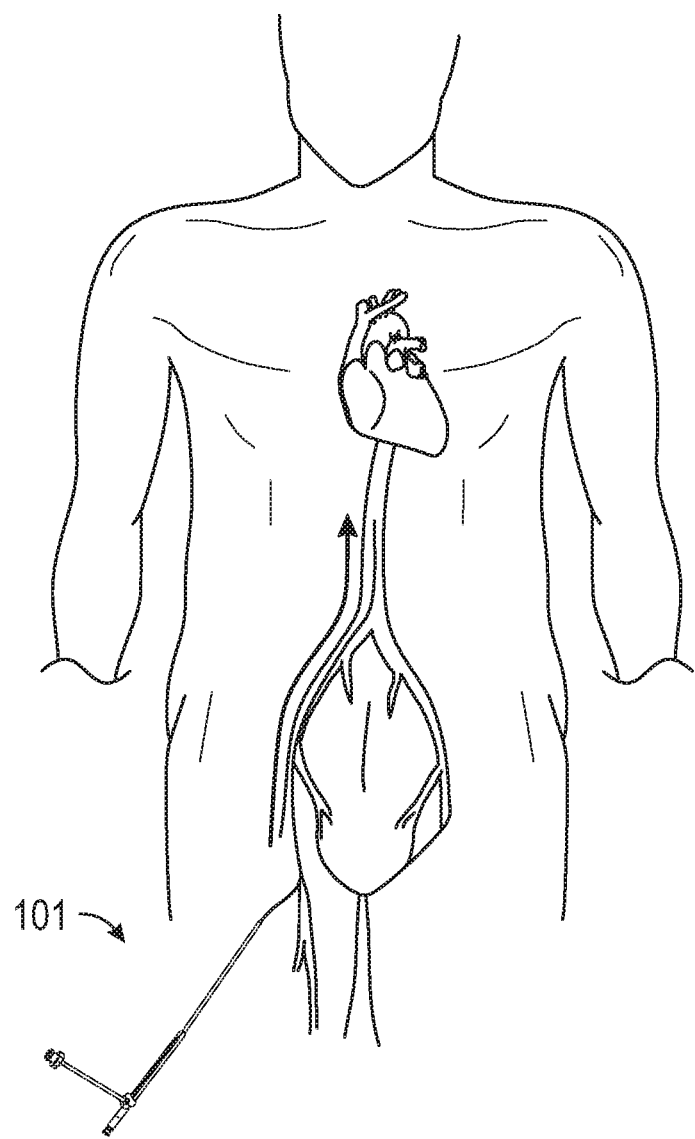
FIGS. 10 A/B/C/D/E show the invention in the anatomy in various configurations.

FIGS. 10a-10e show the presently disclosed catheter system 101 in the human anatomy in various stages of insertion and the corresponding catheter configuration. FIG. 10a shows the catheter system 101 being inserted into an artery remote from the heart, such as in the upper leg. The lengths of the outer tubular member 103 and inner tubular member 203 discussed previously are suitable for the catheter system 101 to traverse an artery all the way up to and into the heart.

FIG. 10b shows the catheter system 101 near a stenotic aortic valve of the heart. The distal end 107 of the outer tubular member 103, in an AL1 configuration, is visible with a guidewire 1002 extending from the outer tubular member 103. In FIG. 10b, the catheter system 101 has been inserted through the vasculature up to the aortic valve of the heart, and the outer tubular member 103 is still fully covering the inner tubular member 203, corresponding to the position of the control ring 109 at the distal end of the control handle 105. The guidewire 1002 is next used to guide the catheter system 101 through (across) the aortic valve into the ventricle. A plurality of holes 1050 may be provided through the wall of the outer tubular member 103 near its distal end 107, where the holes 1050 facilitate improved fluid communication to the proximal (handle) end of the outer tubular member 103 and therefore better measurement of pressure and/or better flow of fluids through the catheter system 101.

FIG. 10c shows the catheter system 101 in the left ventricle. In this figure, the outer tubular member 103 is still fully covering the inner tubular member 203, as the position of the control ring 109 is still at the distal end of the control handle 105. The distal end 107 of the outer tubular member 103 remains in AL1 configuration and is now in its desired location in the ventricular chamber, where the holes 1050 facilitate blood pressure measurement by a sensor at the proximal end of the outer tubular member 103 (discussed below). FIG. 10c represents the stage in the procedure where the catheter system 101 has been inserted into position with the gently curved tip shape of the outer tubular member 103, the guidewire 1002 has been retracted, and the procedure involving the inner tubular member 203 is ready to begin.

Figures 10D, 10E:
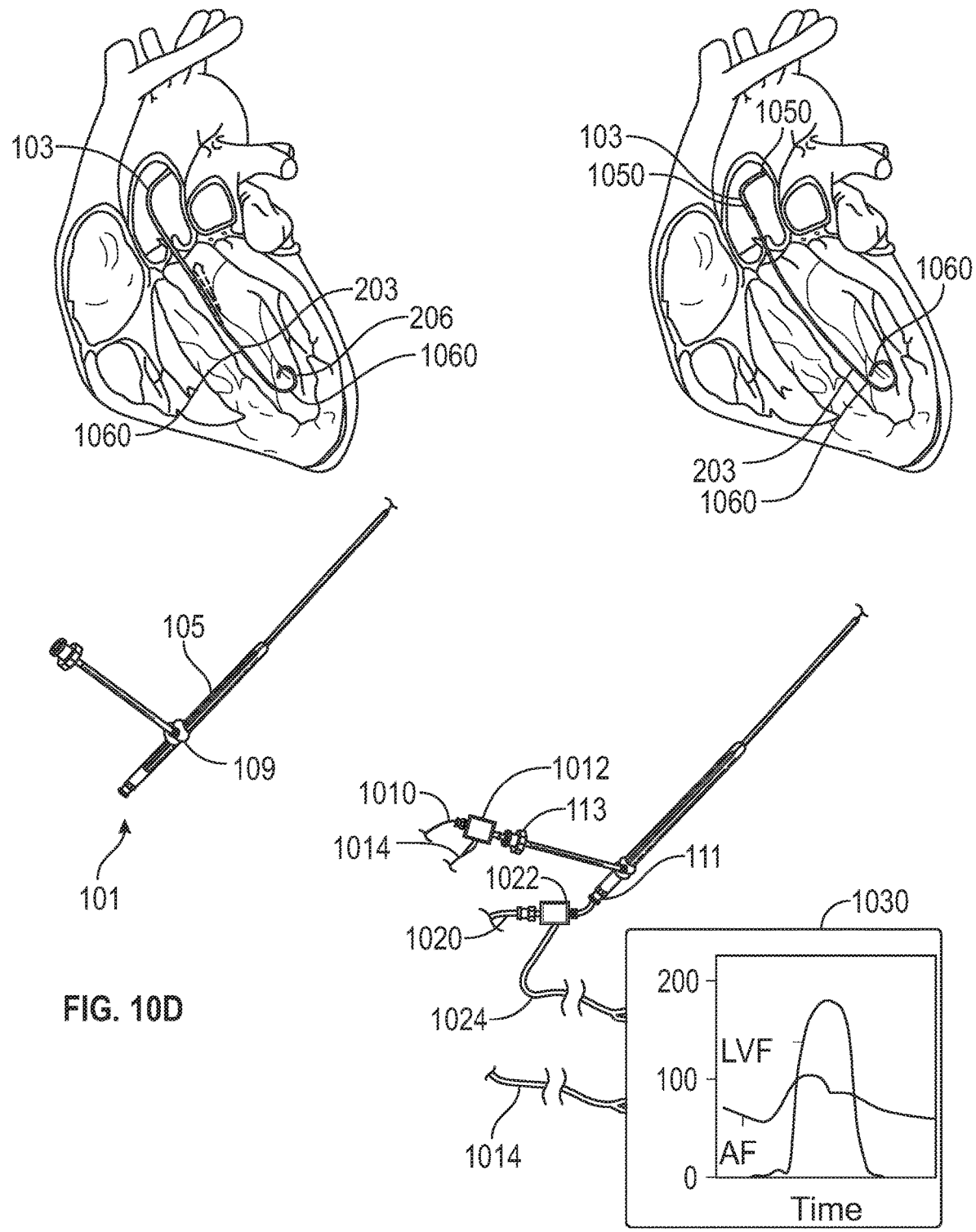

FIG. 10d shows the catheter system 101 being transformed from an AL1 configuration to a pigtail configuration by beginning retraction of the outer tubular member 103. It can be seen in FIG. 10d that the control ring 109 has been moved over halfway toward the proximal end of the control handle 105, which causes the outer tubular member 103 to retract and expose part of the inner tubular member 203. The pigtail shape 205 is now visible at the distal end 206 of the inner tubular member 203. A plurality of holes 1060 may be provided through the wall of the inner tubular member 203 near its distal end 206, where the holes 1060 facilitate improved fluid communication to the proximal (handle) end of the inner tubular member 203 and therefore better measurement of pressure and/or better flow of fluids through the catheter system 101.

FIG. 10e shows the catheter system 101 with the outer tubular member 103 fully retracted back up above the aortic valve. It can be seen in FIG. 10e that the control ring 109 has been moved all the way to the proximal end of the control handle 105, which has caused the outer tubular member 103 to fully retract and expose a maximum amount of the inner tubular member 203. The holes 1050 in the outer tubular member 103 are visible above the aortic valve, where they improve fluid communication between the aortic location and the proximal end of the catheter system 101. The holes 1060 in the inner tubular member 203 are visible in the left ventricle, where they improve fluid communication between the ventricular location and the proximal end of the catheter system 101.

FIG. 10e also shows a pressure transducer 1012 mounted at the side port 113, and a pressure transducer 1022 mounted at the luer 111 to facilitate differential blood pressure measurements, and an inset showing the pressure measurement as it might appear on a viewing instrument. Recall that the luer 111 is in fluid communication with the inside of the inner tubular member 203, and the side port 113 is in fluid communication with the annular space between the outer tubular member 103 and the inner tubular member 203. Thus, the pressure transducer 1012 is measuring pressure at the tip of the outer tubular member 103 above the aortic valve, and the pressure transducer 1022 is measuring pressure at the tip of the inner tubular member 203 in the ventricular chamber. The transducer 1012 provides a signal to the display 1030 via wire 1014, and the transducer 1022 provides a signal to the display 1030 via wire 1024. Alternatively, the transducers may communicate wirelessly with the display and any related computer monitoring system.

FIG. 10e also shows a fluid tube 1010 passing through the pressure transducer 1012 and a fluid tube 1020 passing through the pressure transducer 1022. The fluid tube 1010 is connected to the side port 113 and could be used to introduce a fluid to or withdraw a fluid from the tip of the outer tubular member 103, which in this case is above the aortic valve. The fluid tube 1020 is connected to the luer 111 and could be used to introduce a fluid to or withdraw a fluid from the tip of the inner tubular member 203, which in this case is in the ventricular chamber. Techniques are used to prevent air embolization in the blood stream and air in the tubes 1010 and 1020.

Rather than the transducers 1012 and 1022 to measure blood pressure as shown in FIG. 10, the catheter system 101 may include a sensor mounted near the distal tip of the outer tubular member 103 and/or the inner tubular member 203 to monitor blood pressure (not shown).

The inner tubular member 203 is comprised of a relatively stiff proximal tubular member that is adapted for the outer tubular member 103 to slide over it and have sufficient column strength to avoid buckling. The proximal segment 221 of the inner tubular member 203 can be fused to a more flexible distal segment 222 by any number of means including heat or adhesive bonding. The proximal segment 221 of the inner tubular member 203 may be made of a braid reinforced polymer tubing capable of withstanding high internal pressures without failure. This facilitates the use of a pressure injection system for radiopaque contrast injection into the heart for imaging. The proximal segment 221 of the inner tubular member 203 may be made from a stiffer material such as 304 stainless steel or a reinforced polyimide tube. Alternatively, the inner tubular member proximal segment 221 could have a reinforcing sleeve to provide needed stiffness.

The diameter dimensions of the invention at its proximal end, where it is reinforced or stiffened, can be different than the diameter dimensions, both inner and outer diameters, of the distal segment 222 that enters into the patient or body.

The outer tubular member 103 similarly has a relatively stiffer proximal segment 121 and a more flexible distal segment 122. The proximal segment 121 is designed to withstand buckling as it is advanced and retracted over the outer diameter of the inner tubular member 203. Similar to the inner tubular member 203, the inner and outer diameter dimensions of the distal segment 122 that enters into the body may differ from the portion that interacts with or is in the handle control mechanism.

The catheter system 101 may come in two lengths, such as a standard 100 cm, and a longer 125 cm catheter. Once the sterile catheter system is removed from the sterile packaging, a 150 cm J-tipped guidewire can be inserted into the catheter system 101 (through the interior of the inner tubular member 203) to allow placement of the catheter close to the aortic valve. Once in place, the 150 cm guidewire is removed and a standard 150 cm straight tipped guidewire is placed through the port or luer 111 attached to the base (proximal end) of the handle 105. This port or luer 111 can also enable measurement of left ventricular pressures as discussed above. This is accomplished by attaching an external pressure transducer to this port or, alternatively, incorporating a MEMs or optical pressure sensor into the catheter in fluid communication with the lumen connected to this port.

A second port, the sliding side port 113, is attached to the handle slide mechanism at the control ring 109 and is in fluid communication with the outer tubular member 103. This side port 113 enables the outer tubular member 103 to be flushed with sterile saline or other fluids through the lumen of the outer tubular member 103 (AL shaped catheter). This port also enables measurement of aortic pressures through the lumen of the outer tubular member 103 or AL shaped catheter. In yet another embodiment, additional side holes may be placed in the outer tubular member 103 to facilitate more accurate, or less damped, pressure measurements.

Another application of the invention is for radial PCI. This embodiment provides a single device that could safely, and predictably, be used in place of multiple devices for performing invasive radial angiography. The control handle mechanism converts the shape of the catheter distal tip from one shape to another to perform as a diagnostic catheter for angiography and then safely permit the outer tubular member 103 to be retracted to expose the inner tubular member 203 to safely perform contralateral vessel angiography. In this respect, the control handle mechanism is similar to the transcatheter aortic valve application, although the method of use may vary between procedures. Advantageously, this configuration enables an initial tip configuration to safely navigate through the body's vasculature system. When at the target location, then the tip can be transformed to a more aggressive shape, to more optimally perform the procedure in the coronary arteries. The more aggressive tip shape of the inner tubular member 203, which may be wildly contoured and capable of causing injury during delivery, is sheathed by a more safely shaped outer tubular member 103 until the device is advanced to the treatment zone. The risk of injury is reduced because a safer shape is maintained during delivery.

An alternative embodiment for this invention is for use in interventional cardiology procedures, such as PCIs, where devices are inserted into occluded coronary arteries to reopen them and to provide blood to the heart. In difficult cases, known in the field as complex PCI, extra support is often needed to prevent the guide catheter from backing out of the artery to be treated. In these situations where additional support is needed to deliver either a PTCA balloon or a coronary stent to the target lesion, the inner tubular member 203 is configured to be able to extend from within the outer tubular member 103 into the coronary arteries. The current invention enables this capability faster and easier than the current approach of using multiple devices that require exchanges. In this embodiment, the outer tubular member 103 would replace the function of a standard guide catheter, which typically is placed near the ostium of the vessel to be treated. The inner tubular member 203 is extended from the outer tubular member 103 and is then advanced into the coronary artery to provide extra support. In these procedures, frequent catheter manipulations, including rotating the device, makes it advantageous for the extended inner tubular member 203 to be collapsed so it resides inside the handle control mechanism. This eliminates the proximal segment from extending over the hands of the operator and flopping around during device manipulation.

The previously described control handle mechanism can be used in this application but the movement of the outer catheter would be in the opposite direction. The inner tubular member 203 is attached to and advanced by the control handle mechanism to extend past the outer tubular member 103. A handle embodiment may include provisions to enable a telescoping feature of the handle. This enables an original total catheter length (inner tubular member 203 and outer tubular member 103) that is desirably short for this procedure, for example 90 cm long. When utilizing the telescoping feature for the handle, the inner tubular member 203 assembly is configured so that the telescoping handle can be initially extended proximally (towards the operator and away from the patient); then, during the procedure, the telescoping sections of the handle can be collapsed, thus lengthening the inner tubular member 203 so it may be extended past the outer tubular member 103. In a fully extended position the device length can increase from 90 cm to 125 cm. There can be a means to limit the range of lengths of the inner tubular member 203.

The telescoping feature can be comprised of multiple tubular members designed to slide over each other in this handle embodiment. Each tubular member has a specified diameter that enables it to be slidably positioned over the underlying tubular member having a smaller diameter. There can be two such tubular members, which enable almost doubling the length of the telescoping component of the handle. Additionally, more than two tubular members may be employed in the same fashion to achieve a greater change in length. The distal most tip of the telescoping handle is attached to the proximal end of the catheter inner tubular member 203. The attachment provides for a sealed lumen preventing a leak path for air to enter into the body. A sealing means, such as O-rings, is used to ensure the telescoping handle mechanism is also sealed.

The described invention could be configured to have an inflatable balloon at its distal end to provide even more support. The balloon is attached to either the inner tubular member 203 or the outer tubular member 103. Two balloons, one attached to each tubular member, is also contemplated. It is also advantageous to incorporate a discrete radiopaque marker component at the distal end of one or both of the tubular members 103/203 so that the operator knows the position of the tip of the catheter system 101 in the arterial anatomy. A radiopaque marker may be made of platinum or a platinum alloy, such as 90% platinum and 10% iridium. There are other suitable radiopaque materials or alloys for this function.

The invention may also have the inner tubular member 203 and the outer tubular member 103 loaded, or filled, with a dense radiopaque material to further improve visibility under fluoroscopy or x-ray systems. In this case, a material such as barium sulfate is added to the polymers which ultimately are extruded into tubular form. The ratio of the additive to the parent tubing material may be 80% tubing material and 20% radiopaque additive. Other ratios can be utilized to provide adequate imaging under fluoroscopy.

This embodiment of the invention would also allow the use of a buddy wire system, which can be used for complex PCI. A buddy wire system is when an additional guidewire, is inserted along with the guidewire already in place, is employed through the guide catheter to help facilitate the procedure by providing extra stability or an anchoring function.

This particular embodiment would allow less imaging contrast to be used for complex PCI because there are fewer device exchanges and the inner tubular member 203 is of a smaller diameter lumen, which permits less contrast needed for visualization. Reducing the use of radiopaque contrast for imaging is beneficial to the patient and the hospital staff in the catheter lab.

The present invention simplifies currently practiced procedures by allowing for fewer catheter and guidewire exchanges, thereby reducing risk associated with the procedure. Outlined below are methods utilizing the invention.

Figure 12:
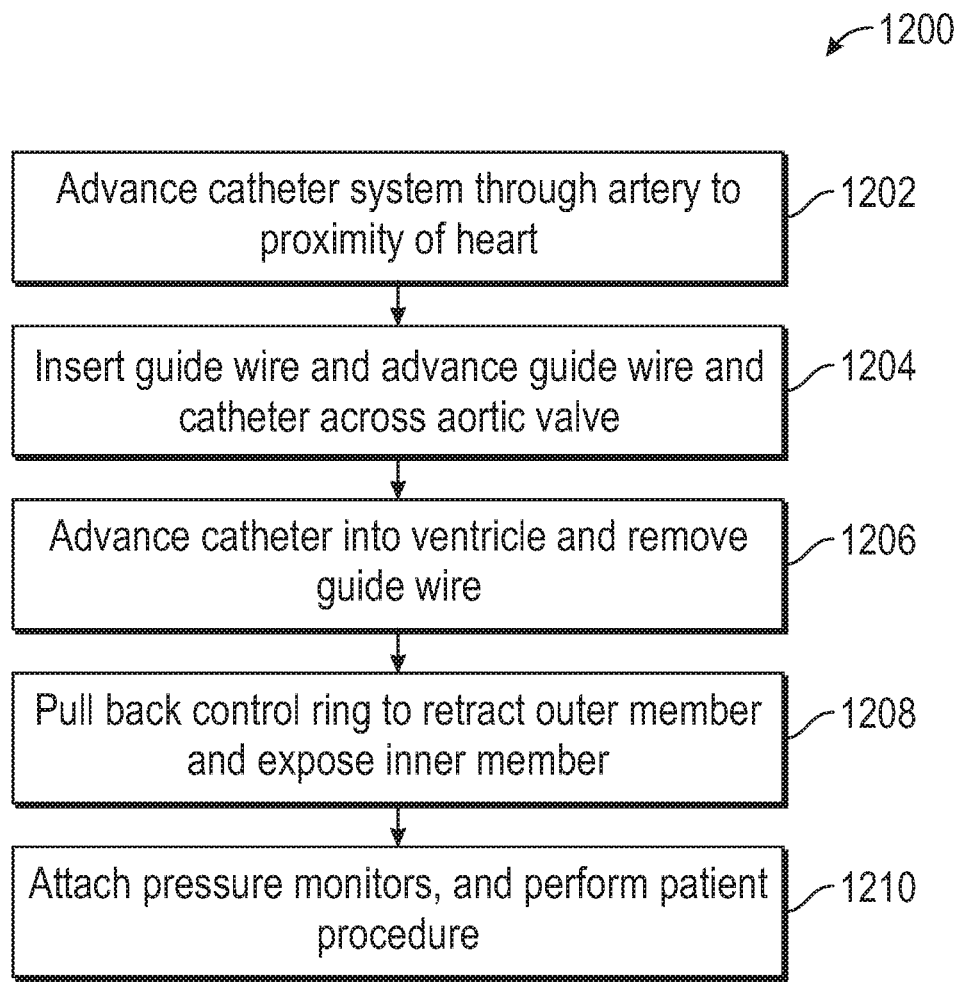
FIG. 12 is a flowchart diagram of a method for employing the disclosed catheter system shown in FIGS. 1-11.

FIG. 12 is a flowchart diagram 1200 of a method for employing the disclosed catheter system 101 shown in FIGS. 1-11. At box 1202, the catheter system 101 is advanced with a preshaped tip, such as an Amplatzer 1 or AL1, through a puncture site into the vasculature, such as the femoral artery, of a patient and to a target site of interest in the body, such as the heart. The step at the box 1202, where the outer tubular member 103 fully covers the inner tubular member 203, is shown in FIG. 10a discussed previously. Once the device is brought close to the aortic valve through the arterial vasculature, at box 1204 the surgeon's left hand (usually index finger and thumb) is used to stabilize the device by holding the control handle mechanism. In addition, the left hand can gently rotate the catheter clockwise or counterclockwise in order to provide different angles for the distal end 107 of the device to cross the stenotic aortic valve. Using the right hand, a straight tipped guidewire 1002, inserted through the Amplatzer lumen, is gently advanced and retracted until it is across the aortic valve. FIG. 10b shows the actions of the box 1204.

Once the guidewire is across the aortic valve, at box 1206 the catheter system 101 is gently advanced into the left ventricle, the straight tipped guidewire 1002 is removed, and the proximal port 111 on the handle 105 is flushed with sterile saline solution. An external pressure transducer is then attached to the port 111 to make a pressure measurement. FIG. 10c shows the actions of the box 1206. At box 1208, holding the control handle 105 with the right hand, the left hand is moved to the handle sliding control ring 109. The right hand is in a fixed position (usually the entire right hand), and the left hand (index finger and thumb) pulls the control ring 109 proximally towards the right hand. Once the handle sliding control ring is fully moved towards the right hand, then the outer tubular member 103, for example the AL1 shaped catheter, is pulled back and exposes the inner tubular member 203, which can be shaped like a pigtail catheter. FIG. 10d shows the outer tubular member 103 partially retracted, and FIG. 10e shows the outer tubular member 103 fully retracted by the movement of the control ring 105 performed at the box 1208.

In this configuration, simultaneous pressure measurements can be made by attaching a second pressure transducer to the side port, which is done after appropriate flushing. For example, differential pressure readings between the left ventricle and aorta can be made by two external transducers, as described above, attached to each of the two ports on the present invention which interrogate each of the two lumens within the device, respectively. Each of the pressure transducers is interrogating separate places in the body, for example, in this case the left ventricle and the aorta. At box 1210, shown in FIG. 10*e*, the catheter system 101 is in position, with the inner tubular member 203 exposed and in position in the left ventricle, and pressure monitors operational. At this point, catheter placement has been completed and the patient procedure (such as a TAVR or a PCI) may be performed.

Using an alternative embodiment, shown in the handle 605 of FIGS. 6 and 8, once in the left ventricle, a control ring mechanism is rotated to unlock the inner tubular member 203 and outer tubular member 103 from a fixed relative position. The operator retracts the ring along a defined longitudinal length moving the ring from one extreme position to the opposite extreme position by moving the control ring mechanism. A hard physical stop prevents movement beyond the defined extreme positions. These two extreme positions of the control ring mechanism correlate with conversion of the catheter tip configuration from one preset shaped to a second preset shape, by retracting the outer tubular member 103 and exposing the inner tubular member 203 distal end. In the handle embodiment of FIG. 7, a push button is used to lock/unlock the control handle configuration.

In the methods discussed above according to this aspect of the invention, the user desirably positions the device easily, safely, and quickly within the left ventricle. The ability to use an initial tip configuration (of the outer tubular member 103) for advancement of the catheter system into the ventricle, and a second tip configuration (of the inner tubular member 203) during performance of the procedure once in place, provides protection against injury to the arteries or the heart wall. The method desirably further includes the step of completing this shape change without the operator having to look directly at the handle mechanism. Methods according to this aspect of the invention afford advantages similar to those discussed above in connection with the apparatus.

In addition, this catheter can then be used for safe placement of the stiff wire for balloon valvuloplasty and transcatheter aortic valve replacement procedures. A stiff guidewire needed to appropriately stabilize and position the valvuloplasty balloon catheter can be inserted into presently disclosed inner tubular member 203 and positioned as desired. The operator would then remove the catheter system 101 while maintaining position of the stiff guidewire. Once the catheter system 101 is fully removed from the guidewire, a valvuloplasty balloon or transcatheter aortic valve can be inserted over the guidewire into position within the anatomy.

It is anticipated that the disclosed invention with its quick catheter tip shape change capability can be applied to other applications that benefit from the need to reduce device exchanges or procedure time. For example, in radial PCI procedures, there is a desire to minimize device exchanges in delicate arteries in the arm. Radial procedures offer patient benefits over traditional femoral artery approaches, reduced recovery time, and fewer access site bleeding complications. Published clinical literature has shown mortality benefits using the radial access approach over the more traditional femoral artery approach. Consequently, the use of radial access PCI procedures have supplanted femoral artery PCI in many labs throughout the world. In addition, many other applications for the disclosed device are envisioned—including applications in the fields of neurology, urology, and peripheral vascular procedures.

While a number of exemplary aspects and embodiments for a rapid catheter tip shape change handle control system have been discussed above, those of skill in the art will recognize modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A concentric two-tube catheter device, said device comprising:
    an inner tubular member having a proximal end attached to a handle body and a distal end with a tip shape configured for a particular medical procedure;
    an outer tubular member concentric with and slidably disposed upon the inner tubular member, said outer tubular member having a proximal end attached to a control ring, and a tip shape configured for placement of the catheter device in a patient;
    a handle assembly comprising the handle body and the control ring, where the control ring is slidably disposed upon the handle body, and where positioning the control ring at a distal end of the handle body causes the outer tubular member to be fully extended and fully cover the inner tubular member, and positioning the control ring at a proximal end of the handle body causes the outer tubular member to be retracted and expose the distal end of the inner tubular member; and
    a side port directly attached to the control ring and configured to slide in unison with the control ring relative to the handle body, the side port in fluid communication with an annular space between the outer tubular member and the inner tubular member, and an end port coupled to a proximal end of the handle body and in fluid communication with an interior of the inner tubular member;
    where the outer tubular member has a bending stiffness greater than that of the inner tubular member, causing the tip shape of the inner tubular member to conform to the tip shape of the outer tubular member when the inner tubular member is fully covered by the outer tubular member.

2. The device according to claim 1 further comprising a first pressure transducer coupled to the end port and configured to monitor a pressure at the distal end of the inner tubular member, and a second pressure transducer coupled to the side port and configured to monitor a pressure at the distal end of the outer tubular member, where the first and second pressure transducers provide signals to a display device for visual display.

3. The device according to claim 1 further comprising a first fluid line coupled to the end port, and a second fluid line coupled to the side port, where the first and second fluid lines are adapted to provide fluids to, or withdraw fluids from, the distal ends of the inner tubular member and the outer tubular member, respectively.

4. The device according to claim 1 wherein the inner tubular member and the end port are adapted to permit a guide wire to be inserted into the end port and advanced to and through the distal end of the inner tubular member.

5. The device according to claim 1 further comprising a stainless steel hypotube concentrically surrounding the proximal end of the inner tubular member inside the handle body, and a flexible slider tube coupling the proximal end of the outer tubular member to the control ring, where the flexible slider tube concentrically surrounds and is slidable relative to the hypotube.

6. The device according to claim 1 wherein the inner tubular member or the outer tubular member, or both, has a plurality of holes formed through a tube wall near its distal end.

7. The device according to claim 1 further comprising a slot in the handle body configured to define limits of travel of the control ring, wherein a distal end of the slot corresponds to a control ring position which causes the outer tubular member to be extended to a position fully covering the distal end of the inner tubular member, and a proximal end of the slot corresponds to a control ring position which retracts the outer tubular member and exposes a maximum desired length of the distal end of the inner tubular member.

8. The device according to claim 6 further comprising a locking feature in the handle body which allows locking the control ring in position relative to the handle body.

9. The device according to claim 8 wherein the locking feature is a slot segment at each end of the slot, where the slot segments are oriented perpendicular to the slot and allow the control ring to be rotated into a locked position.

10. The device according to claim 1 wherein a radiopaque material is provided in a portion of the inner tubular member or the outer tubular member or both, where the radiopaque material improves visibility of the device under fluoroscopy or x-ray.

11. The device according to claim 1 wherein the inner tubular member and the outer tubular member are each comprised of a proximal segment and a distal segment, where the proximal segment of each tubular member has a greater bending stiffness than that of the distal segment of the same tubular member.

12. The device according to claim 1 wherein the tip shape of the outer tubular member is a hook shape configured for advancing the outer tubular member to and across an aortic valve of a patient's heart, and the tip shape of the inner tubular member is a pigtail shape configured for performing a procedure in a ventricle of the heart.

13. A concentric two-tube catheter device, said device comprising:
an inner tubular member having a proximal end attached to a handle body and a distal end with a tip shape configured for a particular medical procedure;
an outer tubular member concentric with and slidably disposed upon the inner tubular member, said outer tubular member having a proximal end attached to a control element, and a tip shape configured for placement of the catheter device in a patient;
a handle assembly comprising the handle body and the control element, where the control element is slidably disposed within a slot in the handle body, and where positioning the control element at a distal end of the handle body causes the outer tubular member to be fully extended and fully cover the inner tubular member, and positioning the control element at a proximal end of the handle body causes the outer tubular member to be retracted and expose the distal end of the inner tubular member;
a side port directly attached to the control element and configured to slide in unison with the control element relative to the handle body, the side port in fluid communication with an annular space between the outer tubular member and the inner tubular member; and
an end port coupled to a proximal end of the handle body and in fluid communication with an interior of the inner tubular member.

14. The device according to claim 13 further comprising a first pressure transducer coupled to the end port and configured to monitor a pressure at the distal end of the inner tubular member, and a second pressure transducer coupled to the side port and configured to monitor a pressure at the distal end of the outer tubular member, where the first and second pressure transducers provide signals to a display device for visual display.

15. The device according to claim 13 further comprising a locking feature in the handle assembly, where the locking feature allows the control element to be locked in position relative to the handle body.

16. The device according to claim 15 wherein the locking feature is a slot segment at each end of the slot in the handle body, where the slot segments are oriented perpendicular to the slot and allow the control element to be rotated into a locked position.

17. The device according to claim 15 wherein the locking feature is a push button on the control element, where depressing the push button allows the control element to be moved along the slot in the handle body, and releasing the push button causes the control element to be locked in position relative to the handle body.

18. A dual-catheter device comprising an inner tubular member, an outer tubular member concentric with and slidably disposed upon the inner tubular member, a control handle assembly including a handle body and a control element, and a side port directly attached to the control element and configured to slide in unison with the control element relative to the handle body, the side port in fluid communication with an annular space between the outer tubular member and the inner tubular member, where sliding the control element along the handle body causes the outer tubular member to be extended or retracted relative to the inner tubular member.

19. The device according to claim 18 further comprising a locking feature in the handle assembly which allows locking the control element in position relative to the handle body.

20. The device according to claim 1 wherein an O-ring is disposed between the control ring and the inner tubular member, the O-ring configured to seal an end of the annular space between the outer tubular member and the inner tubular member, where the O-ring is configured to slide in unison with the control ring relative to the handle body to maintain the seal during a sliding of the control ring relative to the handle body.

* * * * *